US006663880B1

(12) United States Patent
Roorda et al.

(10) Patent No.: US 6,663,880 B1
(45) Date of Patent: Dec. 16, 2003

(54) PERMEABILIZING REAGENTS TO INCREASE DRUG DELIVERY AND A METHOD OF LOCAL DELIVERY

(75) Inventors: Wouter E. Roorda, Palo Alto, CA (US); Vinayak D. Bhat, Sunnyvale, CA (US); Paul M. Consigny, Morgan Hill, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 78 days.

(21) Appl. No.: 09/997,706

(22) Filed: Nov. 30, 2001

(51) Int. Cl.$^7$ ................................ A61F 2/02; A61F 2/06
(52) U.S. Cl. .................. 424/423; 623/1.42; 623/1.43
(58) Field of Search ............................. 623/1.42, 1.43; 424/423

(56) References Cited

U.S. PATENT DOCUMENTS

| | | | |
|---|---|---|---|
| 2,072,303 A | 3/1937 | Herrmann et al. | 128/335.5 |
| 4,977,901 A | 12/1990 | Ofstead | 128/772 |
| 5,021,044 A | 6/1991 | Sharkawy | 604/53 |
| 5,268,164 A | 12/1993 | Kozarich et al. | 424/9 |
| 5,328,471 A | 7/1994 | Slepian | 604/101 |
| 5,464,650 A | 11/1995 | Berg et al. | 427/2.3 |
| 5,578,073 A | 11/1996 | Haimovich et al. | 623/1 |
| 5,605,696 A | 2/1997 | Eury et al. | 424/423 |
| 5,628,730 A | 5/1997 | Shapland et al. | 604/21 |
| 5,667,767 A | 9/1997 | Greff et al. | 424/9.411 |
| 5,670,558 A | 9/1997 | Onishi et al. | 523/112 |
| 5,686,416 A | 11/1997 | Kozarich et al. | 514/15 |
| 5,700,286 A | 12/1997 | Tartaglia et al. | 623/1 |
| 5,716,981 A | 2/1998 | Hunter et al. | 514/449 |
| 5,800,392 A | 9/1998 | Racchini | 604/96 |
| 5,824,049 A | 10/1998 | Ragheb et al. | 623/1 |
| 5,830,178 A * | 11/1998 | Jones et al. | 604/49 |
| 5,830,879 A | 11/1998 | Isner | 514/44 |
| 5,837,313 A | 11/1998 | Ding et al. | 427/2.21 |
| 5,843,172 A | 12/1998 | Yan | 623/1 |
| 5,851,508 A | 12/1998 | Greff et al. | 424/9.411 |
| 5,865,814 A | 2/1999 | Tuch | 604/265 |
| 5,873,904 A | 2/1999 | Ragheb et al. | 623/1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 6,010,530 A | 1/2000 | Goicoechea | 623/1 |
| 6,015,541 A | 1/2000 | Greff et al. | 424/1.25 |
| 6,096,070 A | 8/2000 | Ragheb et al. | 623/1 |
| 6,153,252 A | 11/2000 | Hossainy et al. | 427/2.3 |
| 6,165,212 A | 12/2000 | Dereume et al. | 623/1.13 |

FOREIGN PATENT DOCUMENTS

| | | |
|---|---|---|
| EP | 0 665 023 | 8/1995 |
| EP | 0 970 711 | 1/2000 |
| WO | WO 91/12846 | 9/1991 |
| WO | WO 97/45105 | 12/1997 |
| WO | WO 99/63981 | 12/1999 |
| WO | WO 00/12147 | 3/2000 |
| WO | WO 00/64506 | 11/2000 |
| WO | WO 01/01890 | 1/2001 |
| WO | WO 01/45763 | 6/2001 |

OTHER PUBLICATIONS

Alt et al., *Inhibition of Neointima Formation After Experimental Coronary Artery Stenting: A New Biodegradable Stent Coating Releasing Hirudin and the Prostacyclin Analogue Iloprost*, Circulation Mar. 28, 2000; 101:1453–1458.

(List continued on next page.)

*Primary Examiner*—Carlos A. Azpuru
(74) *Attorney, Agent, or Firm*—Squire, Sanders & Dempsey, L.L.P.

(57) ABSTRACT

A composition and a method for increasing the permeability of membrane junctions or cell membranes for delivery of a drug to target tissues are disclosed. Also disclosed are methods and devices for local drug delivery.

8 Claims, 6 Drawing Sheets

OTHER PUBLICATIONS

Barath et al., *Low Dose of Antitumor Agents Prevents Smooth Muscle Cell Proliferation After Endothelial Injury*; JACC vol. 13, No. 2, Feb. 1989:252A (Abstract).

de Scheerder et al., *Local Methylprednisolone Inhibition Of Foreign Body Response To Coated Intracoronary Stents*, Coronary Artery Disease, Feb. 1996, vol. 7, No. 2, pp. 161–166.

Hurni et al., *Permeability Enhancement in Caco–2 Cell Monolayers by Sodium Salicylate and Sodium Taurodihydrofusidate: Assessment of Effect–Reversibility and Imaging of Transepithelial Transport Routes by Confocal Laser Scanning Microscopy*, The Journal of Pharmacology and Experimental Therapeutics (Jun. 1993) vol. 267, No. 2, pp. 942–950.

Matsumaru et al., *Embolic Materials For Endovascular Treatment of Cerebral Lesions*; J. Biomater. Sci. Polymer Edn, vol. 8, No. 7 (1997), pp. 555–569.

Miyazaki et al., *Antitumor Effect of Implanted Ethylene–Vinyl Alcohol Copolymer Matrices Containing Anticancer Agents on Ehrlich Ascites Carcinoma and P388 Leukemia in Mice*, Chem. Pharm. Bull. 33(6)(1985), pp. 2490–2498.

Miyazawa et al., *Effects of Pemirolast and Tranilast on Intinal Thickening After Arterial Injury in the Rat*; J. Cardiovasc. Pharmacol. (1997), pp. 157–162.

Ohsawa et al., *Preventive Effects of an Antiallergic Drug, Pemirolast Potassium, on Restenosis After Percutaneous Transluminal Coronary Angioplasty*; American Heart Journal (Dec. 1998), pp. 1081–1087.

Park et al., *Anti–inflammatory Stent Coatings: Dexamethasone And Related Compounds*, Semin. Intervent. Cardiol. 1998; 3:191–195.

Shigeno, *Prevention of Cerebrovascular Spasm by Bosentan, Novel Endothelin Receptor*; Chemical Abstract 125:212307 (1996).

van Hoogdalem et al., *3–Amino–1–hydroxypropylidene–1, 1–diphosphonate (APD): A Novel Enhancer Of Rectal Cefoxitin Absorption In Rats*, J. Pharm. Pharmacol. 1989, 41:339–341.

van Hoogdalem et al., *Rectal Absorption Enhancement of Cefoxitin and Desglycinamide Argininè Vasopressin by Sodium Tauro–24, 25–Dihydrofusidate in Conscious Rats*, The Journal of Pharmacology and Experimental Therapeutics 1989, vol. 251, No. 2, pp. 741–744.

* cited by examiner

PERMEABILIZING REAGENTS TO INCREASE DRUG DELIVERY AND A METHOD OF LOCAL DELIVERY

BACKGROUND OF THE INVENTION

1. Field of the Invention

The present invention involves compositions and methods for enhancing the permeability of a vessel wall and/or cell membranes of individual cells to increase the uptake of a local drug delivery.

2. Description of the Background

Despite the general success of percutaneous transluminal interventions such as balloon angioplasty, high restenosis rates continue to be a problem. Various techniques have been used to prevent restenosis, including the use of lasers, application of heat and the use of intravascular stents. However, many of these techniques are still under investigation with mixed results, while others have generally not been successful. Local drug delivery has the prospect of surpassing such techniques, provided sufficient drug uptake into the tissue can be obtained.

The treatment of cancerous tumors is another example of a treatment that could be improved by local drug delivery. In the treatment of tumors, an objective is to administer the cancer drug so that it localizes as much as possible in the tumor itself. Such drugs are commonly administered systemically through the blood stream. Various means are then utilized for causing the drug to bind to the cancerous tumor. Nevertheless, significant portions of the drug administered still circulate through the blood stream. As a result, non-cancerous tissue may be affected by the drug, causing undesirable side effects such a systemic toxicity.

A conventional way to deliver drugs locally has been to use a balloon catheter. The balloon is made from a permeable or semipermeable material, which permits transport of the drug across the balloon surface as a result of an appropriate driving force. This driving force may be provided by several different means. For example, an electrical potential may be applied to the permeable or semipermeable membrane to drive ionic drugs or non-ionic drugs carried in an ionic solution across the membrane in a process known as iontophoresis. Alternatively, high frequency or ultra high frequency (ultrasonic) sound waves supplied by a transducer may be used to transport drugs across the semipermeable membrane in a process known as phonophoresis or (synonymously) sonophoresis.

According to another concept, a modified catheter balloon design includes a balloon having a pair of spaced inflatable lobes. After the balloon is properly positioned, the balloon lobes are inflated by introducing an inflation medium (e.g., saline solution). Inflation of the balloon lobes causes the lobes to expand so that their outer peripheral portions engage the inner surfaces of the vessel walls. This engagement defines an open space, a drug treatment zone, between the lobes. A desired drug is then delivered to the open space, such that the drug is in direct contact with the vessel wall.

According to yet another concept, a catheter is provided having a double walled balloon. An inner balloon is provided which is constructed from an impermeable material such as polyethylene. An outer balloon having a permeable or semipermeable membrane is generally concentric to the inner balloon and extends completely around the inner balloon. The outer balloon is first filled with drug. The inner balloon is then inflated with a standard inflation medium (e.g., saline solution). As a result of inflation of the inner balloon, sufficient pressure is developed against the wall of the outer balloon (in contact with the vessel wall) to drive the drug in the outer balloon through the wall of the outer balloon and toward the vessel wall.

According to yet another concept, a stent can be used for the local delivery of a drug. Implementation of local drug delivery via stents has been achieved with the use of a polymeric matrix coated on the stent. The polymeric coating is impregnated with a drug for in vivo sustained release of the drug.

These methods of local drug delivery are effective in placing a drug in contact with a vessel wall. However, the application of the drug appears to be only superficial. In other words, the drug does not penetrate deep into the tissues of the vessel wall, which is believed to be necessary for optimum results. To pose the problem more concretely, by way of one example, the etiology of restenosis is believed to be the excessive migration and proliferation of vascular smooth muscle cells from the tunica media and adventatia layers of the vascular wall to the intimal layer. In order to efficaciously inhibit or treat restenosis, an effective concentration of the drug must, accordingly, reach the vessel wall's outer layers. With the use of balloons and stents, the exposure of the drug is essentially limited to the intimal layer. The permeability of the vessel wall, therefore, needs to be increased for the local delivery to the sub-layers.

SUMMARY OF THE INVENTION

In accordance with one aspect of the invention, a stent having a radially expandable tubular body and a coating, the coating including a permeabilizing reagent for increasing the permeability of membrane junctions or cell membranes, is disclosed. In one embodiment, the permeabilizing reagent can be selected from the group consisting of a calcium ion chelator, a surfactant, and a receptor-mediated permeabilizing reagent. Furthermore, the permeabilizing reagent can be selected from the group consisting of iminodiacetic acid, nitriloacetic acid, ethylenediaminomonoacetic acid, ethylenediaminodiacetic acid, ethylenediaminotetraacetic acid, sodium taurodihydrofusidate, sodium salicylate, sodium caprate, sodium glycocholate, cholylsarcosine, isopropyl myristate, partially hydrolyzed triglycerides, fatty-acid sugar derivatives, oleic acid derivatives, histamine, bradykinin and its conformational analogs, tumor necrosis factor alpha, nitroglycerine, sodium nitroprusside, diethylamine sodium, 3-morpholinosydnonimine, S-nitroso-N-acetylpenicillamine, and vascular endothelial growth factor and combinations thereof.

In an embodiment, the coating can additionally include a P-glycoprotein system blocker. The P-glycoprotein system blocker can be selected from the group consisting of Pluronic P-85®, verapamil, disulfiram and antisense oligonucleotide complementary to a messenger RNA encoding P-glycoprotein and combinations thereof.

The coating, in addition, can include a drug. The drug can be selected from the group consisting of antineoplastic, antimitotic, antiinflammatory, antiplatelet, antiallergic, anticoagulant, antifibrin, antithrombin, antiproliferative, antioxidant, antimigratory, antiextracellular matrix deposition, pro-apoptotic, nitric oxide donor, pro-angiogenic, and pro-arteriogenic substances and combinations thereof. The coating may also include a polymer.

In accordance with an aspect of the invention, a method of forming a coating for a stent is disclosed, including applying a composition including a permeabilizing reagent and a fluid, and essentially removing the fluid from the composition on the stent to form the coating.

In accordance with another aspect, a method of delivering a drug through a membrane junction or a cell membrane is disclosed, including delivering a permeabilizing reagent to a membrane junction or a cell membrane in a concentration sufficient to increase the permeability of the membrane junction or cell membrane, and delivering a drug to the membrane junction or cell membrane, whereby the drug travels through the membrane junction or cell membrane.

In one embodiment, the permeabilizing reagent is delivered by a stent and/or a catheter. Also, the drug can be delivered by a stent and/or a catheter.

The permeabilizing reagent, in addition, can be a solution including a solute selected from the group consisting of glucose, mannose, maltose, dextrose, fructose, sodium chloride, sodium citrate, sodium phosphate, polyethylene glycol, polyvinyl pyrrolidone and amino acids. Furthermore, the permeabilizing reagent can be selected from the group consisting of iminodiacetic acid, nitriloacetic acid, ethylenediaminomonoacetic acid, ethylenediaminodiacetic acid, ethylenediaminotetraacetic acid, sodium taurodihydrofusidate, sodium salicylate, sodium caprate, sodium glycocholate, cholylsarcosine, isopropyl myristate, partially hydrolyzed triglycerides, fatty-acid sugar derivatives, oleic acid derivatives, histamine, bradykinin and its conformational analogs, tumor necrosis factor alpha, nitroglycerine, sodium nitroprusside, diethylamine sodium, 3-morpholinosydnonimine, S-nitroso-N-acetyl-penicillamine, and vascular endothelial growth factor and combinations thereof.

In accordance with an aspect, a composition for treating restenosis is disclosed, including a permeabilizing reagent and a drug, wherein the permeabilizing reagent increases the permeability of membrane junctions or cell membranes of cells for the delivery of a drug to vascular tissues.

In accordance with another aspect, a method of inhibiting restenosis is disclosed, including applying a permeabilizing reagent to endothelial cells and applying a drug to the area where the permeabilizing reagent is applied.

In accordance with yet another aspect of the present invention, a method of local drug delivery is disclosed, including locally applying a permeabilizing reagent to a selected area of a body tissue, and locally applying a drug to the body tissue.

DETAILED DESCRIPTION

1. Membrane Junctions

Figure 1:
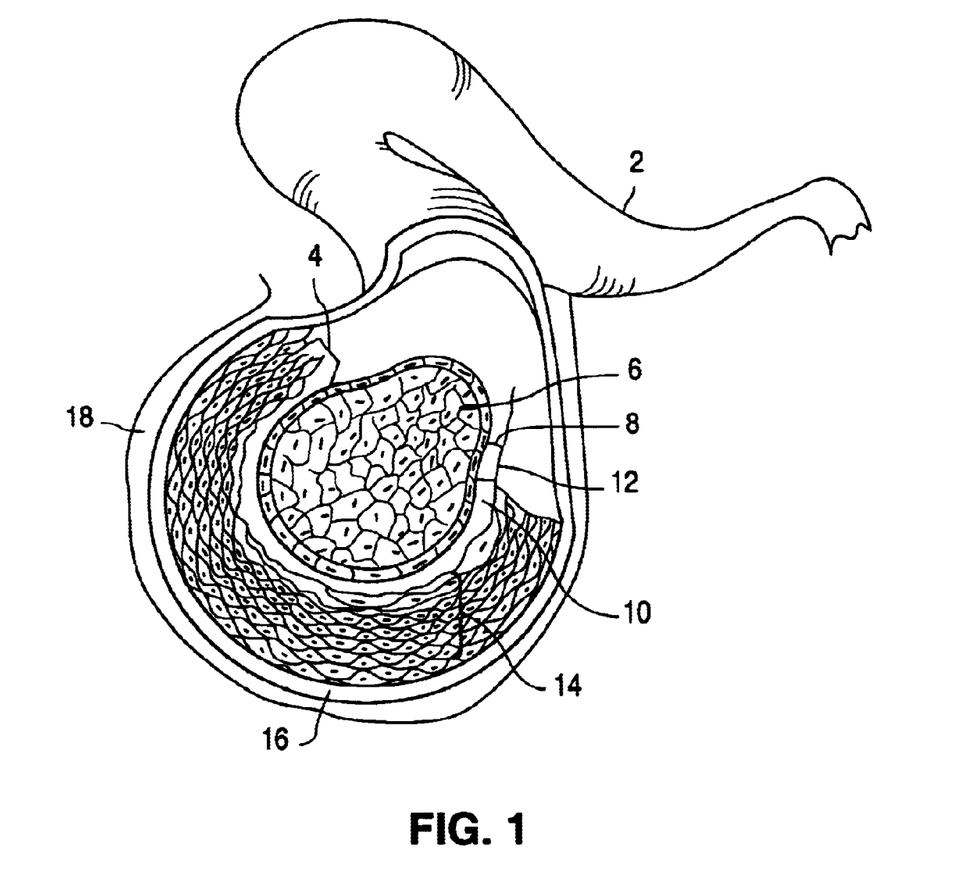
FIG. 1 is a partial cross-sectional view of an artery.

Although certain cell types—blood cells, sperm cells, and some phagocytic cells—are free within the body, may cells, particularly those of epithelial tissues, are knit into tight groups. FIG. 1 illustrates a cross section of an artery 2 showing some cell types that tend to form tight groups. The wall 4 of artery 2 is composed of three distinct layers or tunics (as is the case with all blood vessels except capillaries). These tunics surround a central blood-containing space or a lumen 6. The innermost tunic, which is in contact with blood flowing in lumen 6, is the tunica intima 8. Tunica intima 8 contains the endothelium 10, which lines the lumen of all vessels. Endothelium 10 is composed of endothelial cells, and is a continuation of the endocardial lining of the heart. The flat endothelial cells fit closely together, forming a slick surface that minimizes friction as blood moves through lumen 6. In vessels larger than about 1 mm in diameter, a subendothelial layer 12 of loose connective tissue lies beneath endothelium 10. A middle layer is the tunica media 14, which is composed of smooth muscle cells. The outermost layer is tunica adventitia 16, which is A composed largely of loosely woven collagen fibers. Surrounding tunica adventitia 16 is smooth muscle cell tissue 18.

Adjacent endothelial cells in tunic intima 8 are joined laterally in part by membrane junctions including tight junctions, desmosomes and gap junctions. Although the membrane junctions bind cells close together, the fit is not absolute and therefore there is some extracellular space between the cells known as intercellular clefts.

The membrane junctions not only provide a mechanical bond between cells, but they may provide selective transport mechanisms to allow the endothelial cells to take up nutrients, natural hormones, and other compounds. The membrane junctions, however, can prevent some molecules from passing through the extracellular space between adjacent cells of an epithelial membrane. While the barrier function of tight junctions is desirable, for example, in the case where the blood has become contaminated by bacterial infection, it is undesirable when attempting local intravascular drug delivery. It therefore would be advantageous in many clinical situations to increase the permeability of the membrane junctions.

2. Cell Membranes

Figure 2A:
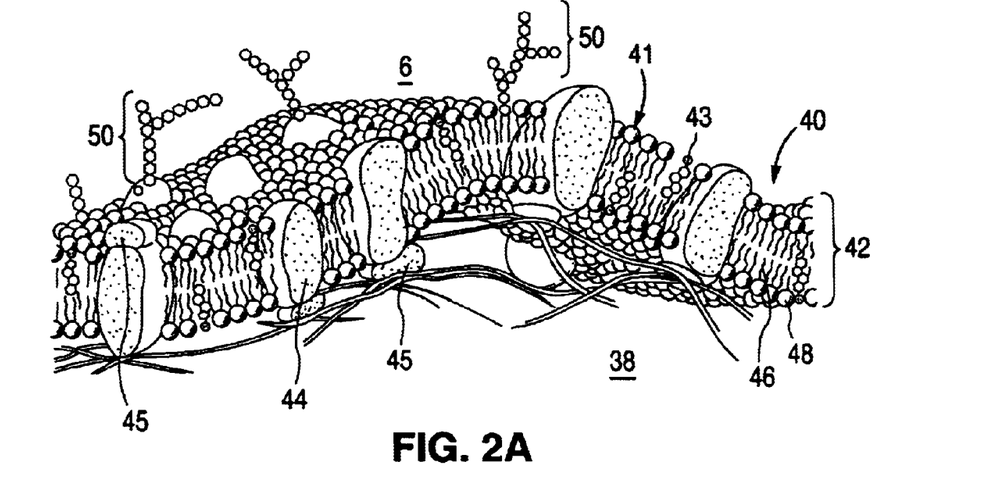
FIG. 2A is a schematic representation of a membrane of a cell lining a vascular wall.

In addition to the membrane junctions, another barrier to drug delivery could be the cell membranes of individual cells. FIG. 2A illustrates a typical cell membrane 40, as would be found, for example, in the cells forming the endothelial cell lining a vascular lumen 6. Cell membrane 40 can act as a barrier to cytoplasm 38. Cell membrane 40 is composed mainly of a lipid bilayer 42, but also has a large number of protein molecules 44 protruding through lipid bilayer 42. Lipid bilayer 42 is a film of lipids only two molecules thick that is continuous over the entire cell surface.

Lipid bilayer 42 is composed almost entirely of phospholipids 41 and cholesterol 43. One portion of the phospholipid 41 and cholesterol 43 molecules is soluble in water (hydrophilic) and another portion of each of these molecules is soluble only in fats (hydrophobic). Because the hydrophobic portions of phospholipid 41 and cholesterol 43 molecules are repelled by water but mutually attracted to each other, they have a tendency to line up as illustrated in FIG. 2A, with the fatty portions 46 in the center of lipid bilayer 42 and the hydrophilic portions 48 projecting away from the center of lipid bilayer 42.

Lipid bilayer 42 is almost entirely impermeable to water and water-soluble substances such as ions, glucose, urea, and others. However, fat-soluble substances, such as oxygen, carbon dioxide and alcohol, can penetrate this portion of membrane 40.

An important feature of this lipid bilayer is that it is a lipid fluid and not a solid. Therefore, portions of the membrane can flow from one point to another in the membrane. For example, proteins floating in the lipid bilayer 42 tend to diffuse to all areas of the cell membrane 40.

As FIG. 2A illustrates, there are globular masses floating in lipid bilayer 42. These are membrane proteins. The membrane proteins include integral proteins 44. Like the lipids, the integral proteins 44 have a fat-soluble portion and a water-soluble portion. However, integral proteins 44 usually have a water-soluble portion on both ends and a fat-soluble portion in the middle. Integral proteins 44 provide structural pathways through which water and water-soluble substances, especially ions, can diffuse between the extracellular fluid and intracellular fluid. Peripheral proteins 45 are normally attached to one of the integral proteins 44. Peripheral proteins 45 function primarily as enzymes.

Membrane carbohydrates 50 may be attached to proteins or lipids of cell membrane 40, and enter into immune system reactions. Membrane carbohydrates 50 often act as receptor substances for binding hormones, such as insulin, that stimulate specific types of activity in the cells.

The rate of membrane penetration by a solute (e.g., drug molecules) is dependent on a variety of factors. These include molecular size of the solute (permeability generally decreases with increasing size), lipid solubility (permeability usually increases with increasing fat or oil stability), and degree of ionization (permeability generally decreases with increased ionization). The diffusion gradient for the solute across the cell membrane also is of great importance. Other factors that can influence transport of a solute include temperature and pH of the extracellular fluid. If these factors and others associated with a particular drug delivery scheme are unfavorable, the rate of membrane penetration by the drug molecules could be very low. It therefore would be advantageous in many clinical situations to increase the permeability of the cell membranes of target cells.

3. Increased Permeability

The term "increased permeability," as used herein, is defined as having a property of allowing an increased mass of a drug to travel through a cellular barrier relative to a cellular barrier that has not been exposed to a permeabilizing reagent. "Cellular barrier" refers to a cellular structure such as a membrane junction and/or a cell membrane that acts to inhibit drug movement into or between cells that would otherwise occur through, for example, active or passive diffusion. "Membrane junction" refers to a junction between cell membranes of adjacent cells such as tight junctions, desmosomes and gap junctions. "Cell membrane" refers to the plasma membrane that encloses a cell's contents such as the cytoplasm and nucleus. For example, the mass of drug taken up by the permeabilized vascular endothelium could be two to ten times greater than a vascular endothelium not contacted by a permeabilizing reagent. For brevity, the embodiments of this invention are explained with reference to the vascular endothelium, although the permeabilizing reagents may increase the permeability of other layers of cells or cell types. Also, the practice of the invention should not be limited to vascular use and the application of the present invention is equally applicable to other tissues or cell linings, such as for the delivery of the drug to the esophagus, urethra, or other biological tissues.

A permeabilizing reagent can be applied to the luminal wall in a concentration sufficient to increase the permeability of the endothelium and/or cell membranes. The application of the reagent is concomitantly or subsequently followed by the administration of a drug to allow the drug to penetrate into the cytoplasm or pass the endothelium lining or other cell build-up, such as cell build-up caused by restenosis. Many different types of compounds may be used as permeabilizing reagents, and various devices may be used to deliver the permeabilizing reagent and/or the drug. Moreover, the invention has many different clinical applications.

An effective amount of the permeabilizing reagent will increase the permeability of the vessel wall and/or cell membranes of individual cells such that sufficient quantities of a drug may pass from within the vasculature into the cytoplasm of individual cells, or through the endothelium and into the adjacent target tissue, where it can exert a therapeutic effect. It is anticipated that a relatively small volume (e.g., 5 mL or less) of permeabilizing reagent is required to achieve this increased permeability.

The amount of drug administered in conjunction with, or after administration of, the permeabilizing reagent is determined on an individual basis and is based, at least in part, on consideration of the individual's size, the specific disease, the severity of the symptoms to be treated, the result sought, and other factors. Standard pharmacokinetic test procedures employing laboratory animals to determine dosages are understood by one of ordinary skill in the art.

4. Classes of Permeabilizing Reagents and Their Effects on the Cell

4A. Hyperosmotic Solutions

Figure 3A:
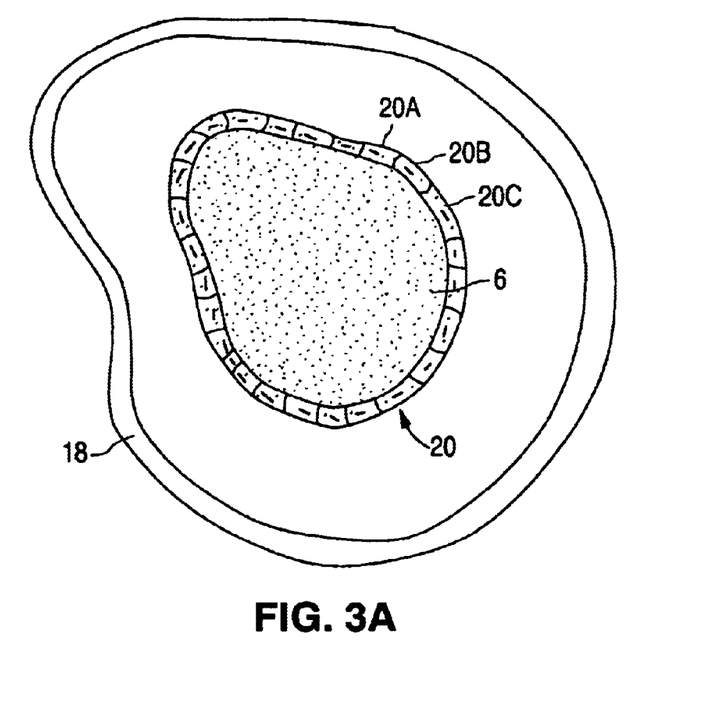
FIG. 3A is an enlarged view of the artery of FIG. 1, showing cells surrounding a hyperosmotic solution present in the lumen of the artery of FIG. 1.
Figure 3B:
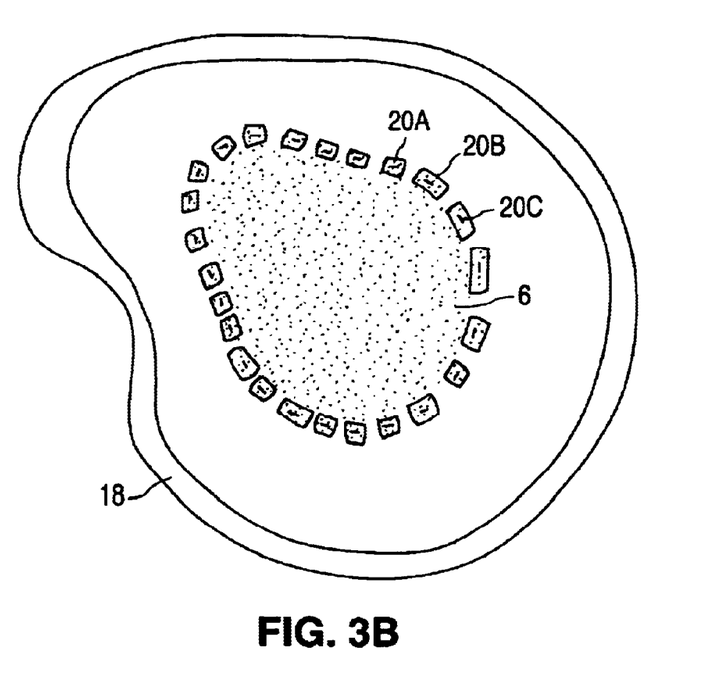
FIG. 3B illustrates the cells of FIG. 3A, after they have reached an equilibrium with the hyperosmotic solution.

Hyperosmotic solutions may be used to temporarily alter the size and shape of the endothelial cells of the vascular wall. Referring now to FIG. 3A, following administration of a solution containing an osmotic agent (in a concentration high enough to provide sufficient osmolality), lumen 6 of artery 2 has a solute concentration higher than the solute concentration inside individual endothelial cells 20 (three of which are labelled as 20A, 20B, and 20C). Due to osmosis, water from within all individual endothelial cells will pass inward toward lumen 6, thereby diluting the fluid in lumen 6. As a result, the endothelial cells surrounding lumen 6 shrink in size, as illustrated in FIG. 3B, increasing the size of the intercellular clefts. Due to the shrinking of the endothelial cells, tissues underlying the endothelial cells are exposed, providing an avenue between endothelial cells for the exposure of a locally provided drug to the media, adventitia and preiadventitia layers.

Since the osmotic agent administered may be excreted by the kidneys or metabolized by other cells in the body, the shrinkage of the endothelial cells by hyperosmotic shock is only a temporary phenomenon (e.g., less than an hour in duration). Therefore, for short duration infusions, a single bolus of a hyperosmotic solution should be sufficient. For longer duration treatment, the osmotic agent may be mixed into the formulation of the drug.

A wide range of compounds are capable of acting as osmotic agents which will shrink the endothelial cells. Of course, the osmolality of a given osmotic agent must be considered. For example, a sodium chloride concentration of 0.9% is approximately iso-osmotic with body fluids. Thus, sodium salts having a concentration greater than 0.9% would be hyperosmotic relative to the interior of an endothelial cell, and would be expected to cause the endothelial cells lining the vascular wall to temporarily shrink. Similarly, a 5% glucose solution is approximately iso-osmotic with body fluids. Thus, sugar solutions greater than 5% in concentration are likewise hyperosmotic relative to the interior of such an endothelial cell, and likewise would be expected to cause the endothelial cell to temporarily shrink.

In principle, any hyperosmotic solution of a biocompatible substance is suitable for use as a permeabilizing reagent. Examples of useful hyperosmotic solutions include solutions of glucose, mannose, maltose, dextrose, fructose and other sugars. Also useful are salt solutions, such as sodium chloride, sodium citrate, and sodium phosphate. Solutions of biocompatible polymers, such as polyethylene glycol (PEG) and polyvinyl pyrrolidone (PVP) and solutions of amino acids are also useful.

4B. Calcium Ion Chelators

Figure 4A:
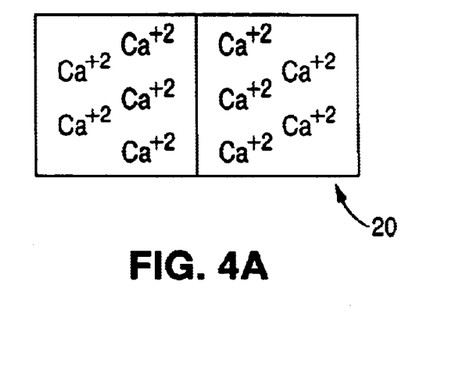
FIG. 4A illustrates cells having normal concentrations of intracellular calcium ions (Ca$^+$)
Figure 4B:
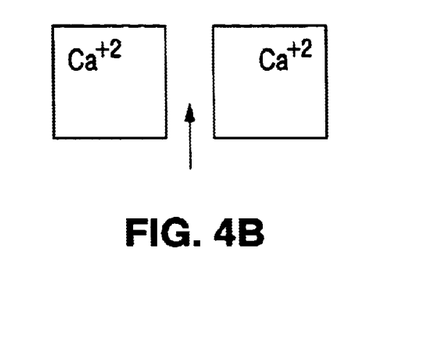
FIG. 4B illustrates the cells of FIG. 4A, wherein the concentration of intracellular calcium ions (Ca$^+$) has been significantly decreased.

Referring to FIGS. 4A and 4B, tight junctions between endothelial cells 20 lining the vascular wall are controlled by chemical signals that are mediated by calcium ion concentration. When calcium ion concentrations decrease, the tight junctions between endothelial cells are opened. Providing a substance that captures calcium ions in the vascular lumen can cause the tight junctions between the endothelial cells to open. Substances that capture calcium ions are known as "calcium ion chelators."

Examples of calcium ion chelators useful for this purpose include iminodiacetic acid (IDA), nitriloacetic acid (NTA), ethylenediaminomonoacetic acid (EDMA), ethylenediaminodiacetic acid (EDDA), and ethylenediaminotetraacetic acid (EDTA). Extensive literature is available concerning the use of EDTA, because it is used as an excipient in many drug compositions. In one embodiment, the concentration of calcium ion chelator in the blood required to decrease intracellular calcium ion concentrations can be from about 0.01 mM to 1 M, for example about 1 mM.

4C. Surfactants

Figure 2B:
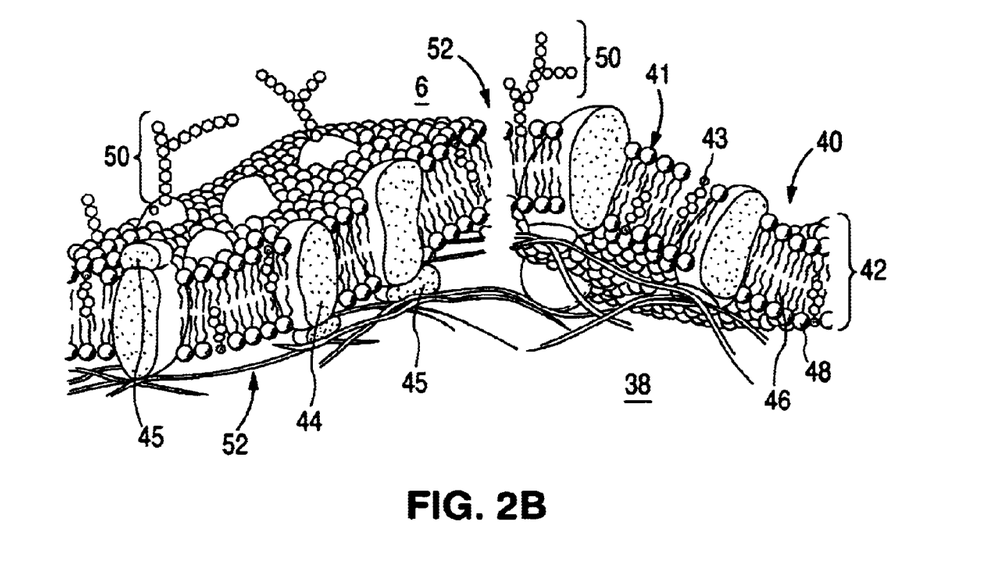
FIG. 2B is a schematic representation of the cell membrane of FIG. 2A, after having been exposed to a surfactant that has increased the permeability of the cell membrane.

In accordance with one embodiment of the invention, a surfactant is used as the permeabilizing reagent. Referring to FIG. 2A, when a surfactant is delivered to a target tissue adjacent to a vascular lumen, by, for example, a stent or catheter, surfactant molecules insert themselves through the outer surface of cell membrane 40, effectively disrupting the dense structure of cell membrane 40 and fluidizing it. The now fluidized cell membrane 40 becomes more permeable (illustratively shown by openings 52 of FIG. 2B). Molecules of a locally delivered drug (e.g., paclitaxel or heparin) can permeate through cell membrane 40. Application of the drug simultaneously with the reagent may be more effective as the duration of permeability is short in time.

Both ionic and non-ionic surfactants may be used in accordance with the invention. Examples of useful ionic surfactants include sodium taurodihydrofusidate, sodium salicylate, sodium caprate, and sodium glycocholate. Examples of useful non-ionic surfactants include cholylsarcosine, isopropyl myristate, partially hydrolyzed triglycerides, fatty-acid sugar derivatives, and oleic acid derivatives. These surfactants may be administered in concentrations ranging from 0.0001% to 10%, more narrowly about 0.001 to 1%, by example about 0.1%. Although ionic surfactants tend to be slightly more effective in fluidizing the membrane, they also tend to be slightly more irritating.

4D. Receptor-Mediated Permeabilizing Reagents

Receptor-mediated permeabilizing reagents also increase the permeability of the membrane of endothelial cells to a drug through their interaction with receptors located on the surface of the endothelial cells of the vascular wall. The interaction between these receptors and the receptor-mediated permeabilizing reagents is presently believed to alter junctional or transport properties between the cells, thereby increasing the permeability of the cell membrane to drug molecules such as antineoplastic, antiinflammatory, and antiplatelet drug molecules. Examples of such receptor-mediated permeabilizing reagents include histamine, bradykinin and its conformational analogs, and tumor necrosis factor alpha (TNF-alpha). TNF-alpha appears to work through a nitric oxide (NO) mediated mechanism, and any compound that increases the local presence of NO, such as nitroglycerine, sodium nitroprusside (SNP), diethylamine sodium (DEA), 3-morpholinosydnonimine (SIN-1), and S-nitroso-N-acetyl-penicillamine (SNAP), is expected to have an effect similar to that of the effect of TNF-alpha. Vascular endothelial growth factor (VEGF) likewise increases the local presence of nitric oxide and nitroprusside, and thus is another such receptor-mediated permeabilizer.

In one exemplary embodiment, histamine and bradykinin can be used at concentrations between 0.01 mM and 0.1M, for example about 100 mM. TNF-alpha should be used at very low concentrations, for example between 0.00001% and 1%, or alternatively between 0.01% and 0.1%. NO donors can be used at higher concentrations, ranging from 0.01 mM to 1 M, or between 1 mM and 0.1 M.

4E. P-Glycoprotein System Blockers Alone or in Conjunction With Other Permeabilizing Reagents One known mechanism by which certain drugs function is by their interaction with a protein that is variously called Multidrug-Resistance 1 protein (MDR 1), Pleiotropic-glycoprotein (P-glycoprotein), P-gp, or P170. Herein, it is referred to as "P-glycoprotein." P-glycoprotein is endogenous in cell membranes, including certain drug resistant cells, multidrug resistant tumor cells, gastrointestinal tract cells, and the endothelial cells that form the blood-brain barrier. P-glycoprotein interacts with certain machinery of the cell in a "P-glycoprotein system." The P-glycoprotein system acts as an efflux pump for the cell. By providing P-glycoprotein system "blockers," which interfere with the efflux pump action of the P-glycoprotein system, a drug is permitted to enter and remain in the cell and exert its desired effect.

Such P-glycoprotein system blockers include, but are not limited to, the surfactant Pluronic P-85® (commercially available from BASF Corporation, Mount Olive, N.J.), the blood pressure medication verapamil, or the anti-alcohol drug disulfiram. In addition, an antisense oligonucleotide complementary to a messenger RNA encoding P-glycoprotein may also be use used to block the P-glycoprotein system. To achieve the desired effect, the P-glycoprotein system blocker can be co-administered with a drug, such that the P-glycoprotein system blocker is present at concentrations ranging from 0.001% solution to 10% (w/v), and more typically at concentrations ranging from 0.1% to 3%.

In accordance with another embodiment of the invention, a permeabilizing reagent other than a P-glycoprotein system blocker is administered first (e.g., an osmotic agent, a calcium ion chelator, a surfactant, and/or a receptor-mediated permeabilizing reagent), followed by administration of the antisense oligonucleotide complementary to the messenger RNA encoding P-glycoprotein at a few selected cells. The first permeabilizing reagent may provide an avenue by which the antisense oligonucleotide may enter the target cell. Once the antisense oligonucleotide is in place in the cell, it prevents the synthesis of P-glycoprotein. Because the cells produce significantly less P-glycoprotein than normal, the P-glycoprotein system for given cells can be disabled for long periods of time. As a result, drugs may be administered to these cells without being exposed to the efflux pumping action of the P-glycoprotein system, and thus will reside in those cells for a longer period of time, increasing the likelihood that the drug will exert its therapeutic effect.

5. Drugs That May be Used in Conjunction With Permeabilizing Reagents

Depending on the type of permeabilizing reagent selected, the drug to be taken up into the target tissue surrounding the vascular endothelium may be administered before, or more usefully, simultaneously with or after administration of the permeabilizing reagent. For example, since the permeabilizing effect of a hyperosmotic solution on the vascular endothelium may last a few hours, the drug may be administered after administration of the hyperosmotic solution. In contrast, if a surfactant is used as the permeabilizing reagent, the drug may be co-administered, since the permeabilizing effect of a surfactant is more transient.

The drug can be for inhibiting the activity of vascular smooth muscle cells. More specifically, the drug can be aimed at inhibiting abnormal or inappropriate migration and/or proliferation of smooth-muscle cells for the inhibition of restenosis. The drug can also include any substance capable of exerting a therapeutic or prophylactic effect in the practice of the present invention. For example, the drug can be for enhancing wound healing in a vascular site or improving the structural and elastic properties of the vascular site. Examples of drugs include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The drug can also fall under the genus of antineoplastic, anti-inflammatory, antiplatelet, anticoagulant, antifibrin, antithrombin, antimitotic, antibiotic, antiallergic, antioxidant and antimigratory substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. The drug can also fall under the genus of antiextracellular matrix deposition, pro-apoptotic, nitric oxide donor, pro-angiogenic, and pro-arteriogenic substances. Other drugs which may be appropriate include alpha-interferon, genetically engineered epithelial cells, rapamycin and dexamethasone.

6. Devices Providing Local Delivery of Permeabilizing Reagent and/or Drug to a Target Tissue In accordance with the invention, the permeabilizing reagent may be delivered to the target tissue by a variety of devices, including, but not limited to, balloon catheters, drug infusion catheters, and stents.

6A. Balloon Catheters

Figure 5:
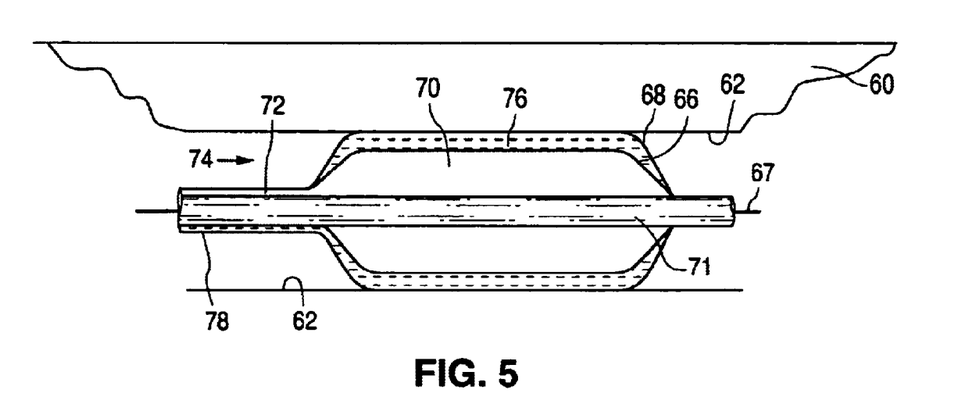
FIG. 5 is a partial cross-sectional view of a balloon catheter for delivering a permeabilizing reagent and/or a drug in accordance with one embodiment of the invention.

FIG. 5 shows local delivery of a permeabilizing reagent to a target tissue 60 adjacent to a vascular wall 62 (e.g., the wall of an artery) through a balloon 74 of an intravascular balloon catheter assembly. Balloon 74 is mounted on a catheter body 71 that may be advanced over a guidewire 67 to a position adjacent to the desired treatment site, which is denoted as target tissue 60. Balloon 74 includes an inner dilatation balloon 66 and an outer balloon 68. Inner dilatation balloon 66 is constructed from a material that is substantially impermeable. Inner dilatation balloon 66 includes an inner chamber 70 which is connected through an inner balloon lumen 72 to the proximal end of the catheter. Outer balloon 68 is generally concentric to inner dilatation balloon 66 and extends completely around inner dilation balloon 66. Outer balloon 68 is constructed from a permeable or semipermeable material and includes a balloon chamber 76 formed between the outer surface of dilatation balloon 66 and the inner surface of balloon 68. Balloon chamber 76 is connected through an outer balloon lumen 78 to a proximal end of the catheter.

To locally deliver a permeabilizing reagent and/or drug, catheter body 71 is advanced through the vascular system until balloon 74 is adjacent to target tissue 60. In one embodiment of the method, chamber 76 of outer balloon 68 is first filled with a permeabilizing reagent. This may be achieved, for example, using an Indeflator® syringe containing a volume of permeabilizing reagent in fluid communication with lumen 78 of outer balloon 68. Chamber 70 of inner balloon 66 is then inflated with a standard inflation medium (e.g., saline solution) provided through lumen 72. In this manner, permeabilizing reagent contained in outer balloon 68 passes through outer balloon 68 and travels radially into contact with vascular wall 62 adjacent to target tissue 60. A sufficient amount of permeabilizing reagent is delivered to increase the permeability of the endothelial cells that form vascular wall 62. After a sufficient amount of permeabilizing reagent is delivered to achieve increased permeability of the endothelial cells lining vascular wall 62, a drug is locally provided to vascular wall 62 adjacent target tissue 60.

According to another embodiment of the method, the permeabilizing reagent and drug are delivered simultaneously through outer balloon 68.

Figure 6:
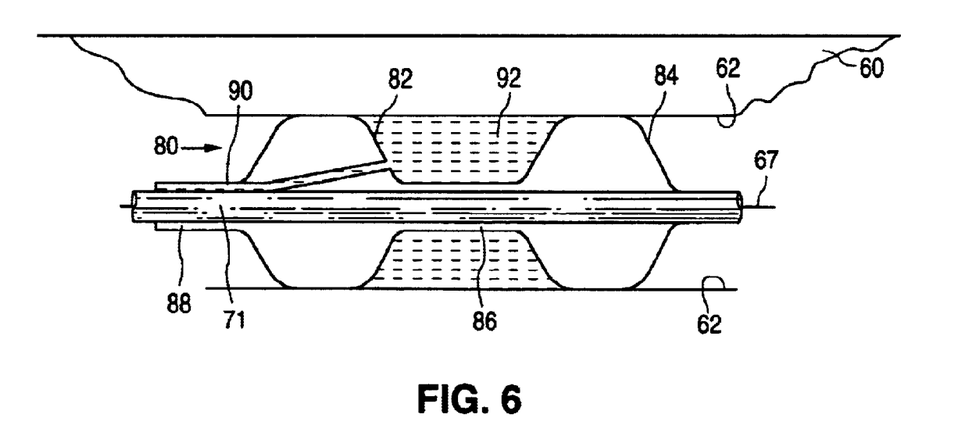
FIG. 6 is a partial cross-sectional view of an alternative balloon catheter for delivering a permeabilizing reagent and/or a drug in accordance with a second embodiment of the invention.

In another embodiment of the invention, illustrated in FIG. 6, a double-lobed balloon 80 is used that has a pair of spaced inflatable balloon lobes 82 and 84. These lobes 80 and 84 are connected by a common interior chamber 86, which is in turn connected to a balloon lumen 88 extending to the proximal end of the catheter. A supply lumen 90 extends to the proximal end of the catheter and is in fluid communication with an area 92 formed between inflated balloon lobes 82 and 84.

After balloon 80 is properly positioned adjacent to target tissue 60, balloon lobes 82 and 84 are inflated by introducing an inflation medium (e.g., saline) through lumen 88 and into interior chamber 86. This inflation causes lobes 82 and 84 to expand so that their outer peripheral portions engage vascular wall 62 adjacent to target tissue 60. This engagement defines a treatment zone 92 between lobes 82 and 84. A permeabilizing reagent is then introduced through lumen 90 and into treatment zone 92 so that the permeabilizing reagent is in direct contact with the endothelial cells of vascular wall 62. Following administration of a sufficient concentration of the permeabilizing reagent to achieve the increased permeability of vascular wall 62, a drug is administered through lumen 90 and into treatment zone 92. The drug can come into contact with the target tissue through the increased permeability of vascular wall 62.

6B. Drug Infusion Catheters

Figure 7:
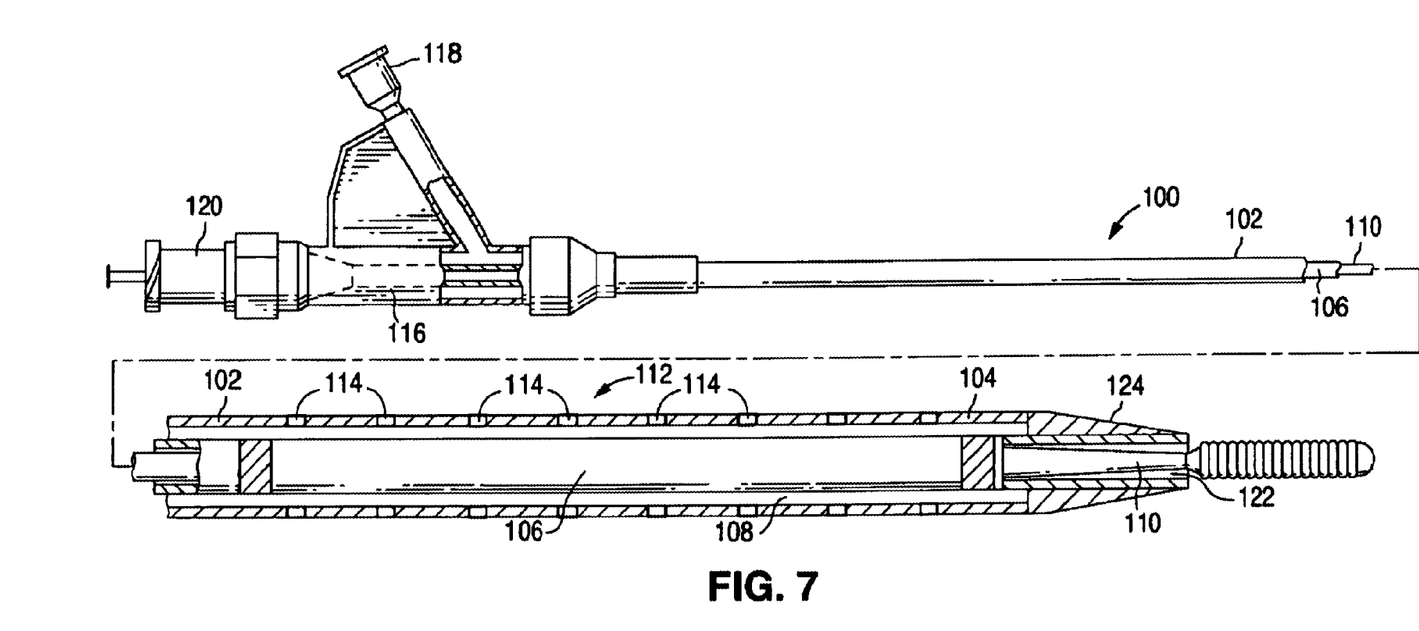
FIG. 7 is a partial cross-sectional view of a drug infusion catheter for delivering a permeabilizing reagent and/or a drug in accordance with a third embodiment of the invention.

In yet another embodiment of the invention, a drug infusion catheter, rather than a balloon catheter, is used to deliver the permeabilizing reagent and/or the drug. An example of such a drug infusion catheter is shown in FIG. 7. In general, a catheter assembly 100 includes an elongated tubular body 102 having an outer tubular member 104 and an inner tubular member 106 concentrically disposed within outer tubular member 104 and defining an annular lumen 108 therebetween. Inner tubular member 106 is adapted to receive a guidewire 110 which facilitates the advancement of catheter assembly 100 to place an operative distal portion 112 thereof at a desired site in the patient's vascular system. Outer tubular member 104 is provided with a plurality of flow passageways 114 in operative distal portion 112, which are spaced along the length thereof. The transverse cross-sectional area, i.e., the discharge area, of passageways 114 increases with each successive passageway in the distal direction. Uniform spacing between the centerline of individual passageways 114 is provided. Advantageously, this design provides a uniform flow of permeabilizing reagent and/or drug to the exterior of outer tubular member 104. This feature may be particularly desirable, for example, in local delivery of a small volume of a drug at low flow rates (e.g., 0.1–1.5 mL/hr).

The proximal end of catheter assembly 100 is provided with a two-arm adapter 116, having one arm 118 for introducing permeabilizing reagent and/or drug into annular lumen 108 and another arm 120 for directing guidewire 110 into a lumen 122 within inner tubular member 106.

A flexible tip 124 is provided on the distal end of tubular body 102 to lessen the trauma caused by the introduction of the catheter into the patient's blood vessel. The tip is formed of a softer, more resilient plastic material than either inner tubular member 106 or outer member 104. Flexible tip 124 closes off and seals the distal end of annular lumen 108. Further details regarding this drug delivery catheter may be found in commonly assigned U.S. Pat. No. 5,021,044.

Of course, the balloon catheter design and drug infusion catheter designs discussed above are merely exemplary; other catheter designs, and indeed other local delivery devices, may be used in accordance with the invention.

6C. Drug Delivery Stents

According to another embodiment of the present invention, both the permeabilizing reagent and/or the drug of interest are locally delivered by a drug delivery stent. It should be understood by one of ordinary skill in the art that a variety of application routes are possible. For example, both the drug and reagent can be applied via a stent. Alternatively, the reagent can be applied by the catheter or balloon and the drug applied via the stent. Yet in another embodiment, the reagent can be administered systemically and the drug applied via the stent.

Figure 8:
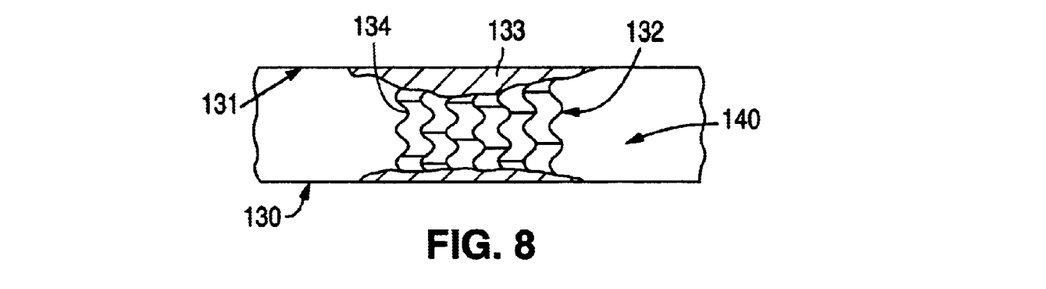
FIG. 8 is a cross-sectional side view of a stent implanted in a vascular lumen.

FIG. 8 illustrates an exemplary drug delivery stent implanted in a vascular lumen 130 defined by vascular wall 131. A stent 132 includes a plurality of struts 134. Struts 134 define a generally cylindrical stent body having an outer surface in contact with the vascular wall 131 and an inner surface in contact with a fluid stream 140 flowing through lumen 130.

Figure 8A:
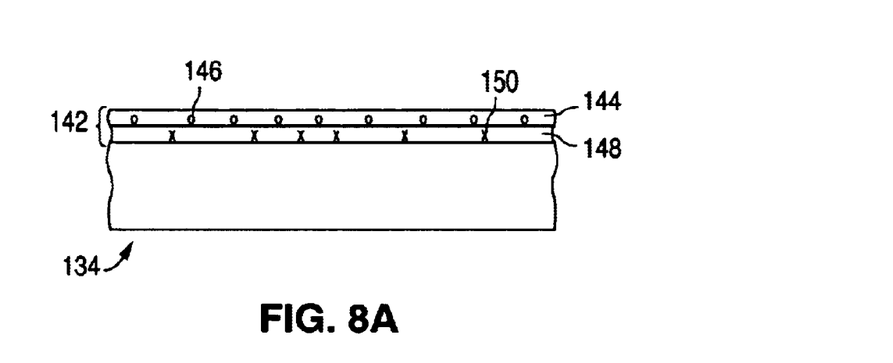
FIG. 8A is a cross-sectional view of a strut of a stent having a polymer coating including two sublayers.

FIG. 8A illustrates a cross-sectional view of strut 134 of stent 132. A polymer layer 142 can be deposited on the outer surface of strut 134. Polymer layer 142 includes a first sublayer 144 (e.g., polycaprolactone), which contains a permeabilizing reagent 146, and is disposed above a second sublayer 148 (e.g., polysiloxane), which contains a drug 150. Two distinct layers are useful, since the composition of the polymer layer may be selected to influence the rate of release of the permeabilizing reagent or drug. With such a layering of permeabilizing reagent 146 and drug 150 in sublayers 144 and 148, essentially all of the permeabilizing reagent 146 is released from stent 132 before drug 150 is released from stent 132. Accordingly, the endothelial cells of the vascular wall will have increased permeability so that drug 150 may be delivered in increased concentration to target tissue 133.

Figure 8B:
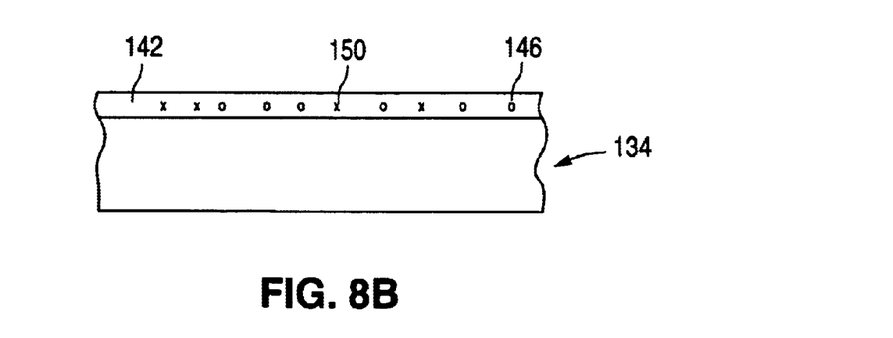
FIG. 8B is a cross-sectional view of a strut of a stent, having a polymer coating, wherein a permeabilizing reagent and a drug are intermixed in the polymer coating.

In yet another embodiment, illustrated in FIG. 8B, permeabilizing reagent 146 and drug 150 are intermixed in a single polymer layer 142 so as to effect a simultaneous local delivery of permeabilizing reagent 146 and drug 150 to the endothelial cells of vascular wall 131.

Of course, in embodiments where a stent is used to locally deliver both the permeabilizing reagent and the drug, certain compatibility factors must be considered. It is essential that the polymer, the permeabilizing reagent, and the drug be mutually compatible. Moreover, the polymer and the permeabilizing reagent should not chemically alter the therapeutic nature of the drug.

Representative examples of polymers that can be used to coat a stent in accordance with the present invention include ethylene vinyl alcohol copolymer (commonly known by the generic name EVOH or by the trade name EVAL), poly (hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly (iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

Examples of stents include self-expandable stents, balloon-expandable stents, and stent-grafts. The underlying structure of the stent can be of virtually any design. The stent can be made of a metallic material or an alloy such as, but not limited to, cobalt chromium. alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Stents made from bioabsorbable or biostable polymers could also be used with the embodiments of the present invention

7. Treatment of Disease

The methods and structures shown herein may be used for the treatment of various diseases. "Treatment of disease" includes: (i) preventing the disease, that is, causing the clinical symptoms of the disease not to develop; (ii) inhibiting the disease, that is, arresting the development of clinical symptoms; and/or (iii) relieving the disease, that is, causing the regression of clinical symptoms. For example, the present invention may be used to treat ischemia. Such a treatment may include selecting an (ischemic) target tissue, and contacting an arterial wall adjacent the target tissue with a balloon catheter containing EDTA. A pro-angiogenic or pro-arteriogenic drug, such as VEGF, is then introduced to the arterial wall through the balloon catheter.

In accordance with another aspect of the invention, the present invention may be used for the treatment of restenosis. For example, for the purpose of preventing restenosis, an anti-proliferative drug (e.g., rapamycin or decetaxel) can administered. In conjunction or prior to the administration of the drug, the surfactant sodium taurodihydrofusidate is administered as a permeabilizing reagent.

While particular embodiments of the present invention have been shown and described, those skilled in the art will appreciate that changes and modifications can be made without departing from the invention in its broader aspect. For example, many balloon catheters, drug infusion catheters and stents are useful in practicing the invention. Many different combinations of permeabilizing agents and drugs are possible. Therefore, the appended claims are to encompass within their scope all such changes and modifications as fall within the scope of this invention.

What is claimed is:

1. A stent comprising a radially expandable tubular body and a coating, the coating including a permeabilizing reagent for increasing the permeability of membrane junctions or cell membranes.

2. The stent of claim 1, wherein the permeabilizing reagent is selected from the group consisting of a calcium ion chelator, a surfactant, and a receptor-mediated permeabilizing reagent.

3. The stent of claim 1, wherein the permeabilizing reagent is selected from the group consisting of iminodiacetic acid, nitriloacetic acid, ethylenediaminomonoacetic acid, ethylenediaminodiacetic acid, ethylenediaminotetraacetic acid, sodium taurodihydrofusidate, sodium salicylate, sodium caprate, sodium glycocholate, cholylsarcosine, isopropyl myristate, partially hydrolyzed triglycerides, fatty-acid sugar derivatives, oleic acid derivatives, histamine, bradykinin and its conformational analogs, tumor necrosis factor alpha, nitroglycerine, sodium nitroprusside, diethylamine sodium, 3-morpholinosydnonimine, S-nitroso-N-acetyl-penicillamine, and vascular endothelial growth factor and combinations thereof.

4. The stent of claim 1, wherein the coating additionally includes a P-glycoprotein system blocker.

5. The stent of claim 4, wherein the P-glycoprotein system blocker is selected from the group consisting of Pluronic P-85®, verapamil, disulfiram and antisense oligonucleotide complementary to a messenger RNA encoding P-glycoprotein and combinations thereof.

6. The stent of claim 1, wherein the coating additionally includes a drug.

7. The stent of claim 6, wherein the drug is selected from the group consisting of antineoplastic, antimitotic, antiinflammatory, antiplatelet, antiallergic, anticoagulant, antifibrin, antithrombin, antiproliferative, antioxidant, antimigratory, antiextracellular matrix deposition, pro-apoptotic, nitric oxide donor, pro-angiogenic, and pro-arteriogenic substances and combinations thereof.

8. The stent of claim 1, wherein the coating additionally includes a polymer.

* * * * *